United States Patent
Carpenter

(10) Patent No.: US 11,484,661 B2
(45) Date of Patent: Nov. 1, 2022

(54) SELF-RIGHTING DEVICE FOR A MEDICAMENT DELIVERY DEVICE VERTICAL POSITIONING

(71) Applicant: SHL MEDICAL AG, Zug (CH)

(72) Inventor: Lucas Carpenter, New Taipei (TW)

(73) Assignee: SHL MEDICAL AG, Zug (CH)

( * ) Notice: Subject to any disclaimer, the term of this patent is extended or adjusted under 35 U.S.C. 154(b) by 504 days.

(21) Appl. No.: 16/563,242

(22) Filed: Sep. 6, 2019

(65) Prior Publication Data
US 2020/0155768 A1  May 21, 2020

(30) Foreign Application Priority Data
Nov. 21, 2018 (EP) ..................... 18207448

(51) Int. Cl.
| | | |
|---|---|---|
| *A61M 5/315* | (2006.01) | |
| *A61M 5/31* | (2006.01) | |
| *F16M 11/20* | (2006.01) | |

(52) U.S. Cl.
CPC ...... *A61M 5/31596* (2013.01); *A61M 5/3146* (2013.01); *F16M 11/2035* (2013.01); *A61M 2005/3123* (2013.01); *A61M 2205/10* (2013.01); *A61M 2205/21* (2013.01); *A61M 2205/3368* (2013.01); *A61M 2205/581* (2013.01); *A61M 2205/587* (2013.01); *A61M 2205/8206* (2013.01); *A61M 2209/084* (2013.01); *F16M 2200/044* (2013.01)

(58) Field of Classification Search
CPC ............ A61M 5/31596; A61M 5/3146; A61M 2005/3123; A61M 2205/10; A61M 2205/21; A61M 2205/3368; A61M 2205/581; A61M 2205/587; A61M 2205/8206; A61M 2209/084; F16M 11/2035; F16M 2200/044
See application file for complete search history.

(56) References Cited

U.S. PATENT DOCUMENTS 3,921,331 A * 11/1975 Schatz ..................... A63H 3/28
446/297
4,043,334 A    8/1977 Brown et al.
(Continued)

FOREIGN PATENT DOCUMENTS

EP    3378515 A1 *  9/2018  .............. A61M 5/32
EP    3378515 A1     9/2018
(Continued)

*Primary Examiner* — Terrell L McKinnon
*Assistant Examiner* — Ding Y Tan
(74) *Attorney, Agent, or Firm* — McDonnell Boehnen Hulbert & Berghoff LLP

(57) ABSTRACT

A self-righting device is disclosed having a support body for supporting a medicament delivery device, where the support body has a mass, a center of gravity (G) and a shape such that the self-righting device, when positioned on a substantially horizontal surface, moves from an unbalanced position to an upright position. The self-righting device can also have a mechanical adaptor configured for attachment to the support body and for holding an elongated medicament delivery device at an angle less than 30 degrees from a vertical axis when the self-righting device is in the upright position. An assembly of a self-righting device and an elongated medicament delivery device is also provided.

11 Claims, 9 Drawing Sheets

(56) References Cited

U.S. PATENT DOCUMENTS

| | | | |
|---|---|---|---|
| 5,797,885 A * | 8/1998 | Rubin | A61M 5/3213 |
| | | | 604/263 |
| D797,929 S * | 9/2017 | Davis | D24/130 |
| 10,195,344 B2 * | 2/2019 | Ferriter | A61M 5/31596 |
| D842,464 S * | 3/2019 | Davis | D24/130 |
| 10,688,251 B2 * | 6/2020 | Davis | A61M 5/3134 |
| 2004/0198159 A1 * | 10/2004 | Xu | A63H 33/26 |
| | | | 446/325 |
| 2011/0060274 A1 * | 3/2011 | Kuhn | A61M 5/284 |
| | | | 604/82 |
| 2016/0067422 A1 * | 3/2016 | Davis | A61M 5/3134 |
| | | | 604/192 |
| 2018/0093040 A1 * | 4/2018 | Thorne, Jr. | A61M 5/19 |
| 2020/0011477 A1 * | 1/2020 | Wartersian | F16M 11/2035 |
| 2021/0146057 A1 * | 5/2021 | King | A61M 5/2033 |

FOREIGN PATENT DOCUMENTS

| | | | | |
|---|---|---|---|---|
| GB | 2443257 A * | 4/2008 | | |
| TW | M376430 * | 3/2010 | | |
| WO | 2008/087071 A1 | 7/2008 | | |
| WO | WO-2008087071 A1 * | 7/2008 | | A61M 11/007 |
| WO | 2016/040126 A1 | 3/2016 | | |
| WO | 2017/086607 A1 | 5/2017 | | |

* cited by examiner

SELF-RIGHTING DEVICE FOR A MEDICAMENT DELIVERY DEVICE VERTICAL POSITIONING

CROSS REFERENCE TO RELATED APPLICATIONS

The present application claims priority to European Patent Application No. 18207448.4 filed Nov. 21, 2018 which is herewith incorporated by reference into the present application.

TECHNICAL FIELD

The present disclosure generally relates to a self-righting supporting device for holding a medicament delivery device in a vertical position. In particular, the self-righting device comprising a support body for supporting the medicament delivery device, and an assembly comprising a self-righting device and an elongated medicament delivery device, are provided.

BACKGROUND

There is a variety of diseases which require regular treatment by an injection or an inhalation of a medicament. Often such treatments are performed by patients themselves, sometimes once or several times a day. The devices on the market for self-administering doses of medicament are widely vary depending on a kind of medicament to be delivered to the patient. Some kind of medicaments, such as for example, Bydureon, a drug used against a diabetes, shall be properly shacked during some time prior to delivery to a patient. Another drugs might be unstable and require a mixing or dissolving of an active substance just prior to the delivery. Some types of medicaments can be stored for a long time and may be filled in containers, such as cartridges, syringes, ampoules, canisters or the like, containing a ready-to-use medicament in liquid state. However, some types of medicaments are a mixture of two substances, typically a medicament agent (such as lyophilized, powdered or concentrated liquid) and a diluent (such as water, dextrose solution or saline solution). These types of medicaments cannot be pre-mixed and stored for a long time because the medicament agent is unstable and will lose its effect quickly due to degradation. Hence, a user has to perform the mixing within a limited time period prior to the delivery of a dose of medicament by manually operating a medicament delivery device. During the mixing, the container may comprise both gas and medicament, and the escaping gas might expel some amount of the medicament. In this case, the dose of medicament may be smaller than intended.

In order to facilitate the mixing, a number of containers for medicament have been developed comprising at least two chambers, known as multi-chamber containers. Multi-chamber containers typically comprise a first chamber containing the medicament agent and at least one second chamber containing the diluent. These chambers may be sealed off with a stopper such that the medicament agents cannot be mixed when stored and do not become degraded. When the medicament agent is to be mixed shortly before administering and the stopper is moved, redirecting passages are opened between the chambers. The passages allow the mixing of the medicament agent and the diluent. After sufficient mixing, the medicament is ready for delivery.

There is a risk that the medicament delivery device due to its shape falls or rolls away. This in turn risks damage to the medicament delivery device. Therefore, it is desired to avoid this risk and provide a holder or a support. The medicament delivery devices with multi-chambers containers often requires priming of the medicament delivery device before being used. This means that all gas or air bubbles in the medicament are to be evacuated. Some medicaments requires a couple of minutes shaking prior to delivery to ensure a proper mixing of ingredients. Some medicaments due to higher viscosity need to be primed for a longer period.

U.S. Pat. No. 5,797,885 A discloses an apparatus and a method for recapping of syringe needles situated on a proximal end. The apparatus comprises a cap holder with a base and a weight distribution such that a cap retained in the cap holder is always oriented in an upright position with the upper end thereof being opened.

U.S. Pat. No. 4,043,334 discloses a self-righting syringe protector for a syringe after its filling with a medicament in form of a cap to prevent leakage and contamination. The cap has a tubular coupler which automatically points upwardly. A U.S. Pat. No. 5,797,885 discloses an apparatus for recapping the used syringe needle for protection of the medical professionals from injuries.

An International application WO 2016/040126 discloses a self-righting cap developed for receiving syringes, small-bore tube connectors, catheters or enteral feeding tubes to prevent their misconnection.

An International application WO 2017/086607 discloses a syringe safety cap assembly and, particularly, a syringe safety cap assembly, which can prevent a user from being hurt when inserting a syringe needle into a cap and can also fundamentally block the reuse of a syringe or a syringe needle, which are to be discarded.

A number of different supplemental or accessory type's devices are known on the market which are to be used together with the automatic medicament delivery devices for a self-administration. Those supplemental devices are able to record information about the various times when the medicament is to be administrated, quantity to be delivered and the other parameters.

SUMMARY

In the present disclosure, when the term "distal" is used, this refers to the direction pointing away from a dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

One object of the present disclosure is to provide a supporting device with a self-righting body for supporting a medicament delivery device, which self-righting supporting device improves user experience and can support the medicament delivery device in a substantially vertical position for the required time.

A further object of the present disclosure is to provide a supporting self-righting device body for supporting a medicament delivery device, which the supporting self-righting device due to keeping the medicament delivery device in up-right position improves priming of the medicament delivery device.

A still further object of the present disclosure is to provide a self-righting device for supporting a medicament delivery device, which self-righting device improves quality of mixing of two substances in the medicament delivery device achieving a homogenous ready-to-use medicament.

A still further object of the present disclosure is to provide a supporting medicament delivery device self-righting device, which self-righting device facilitates gas escape from the medicament delivery device via its up-right oriented proximal end.

A still further object of the present disclosure is to provide a medicament delivery device self-righting supporting device a, which self-righting device body enables support of different types and shapes of elongated medicament delivery devices.

A still further object of the present disclosure is to provide a medicament delivery device supporting self-righting device, which self-righting device improves accuracy of the medicament dose delivery.

A still further object of the present disclosure is to provide a medicament delivery device supporting self-righting device, which self-righting device solves two or more of the foregoing functions in combination.

A still further object of the present disclosure is to provide an assembly comprising a supporting self-righting device and a medicament delivery device while supported, which assembly solves one, several or all of the foregoing objects.

According to one aspect, there is provided a self-righting device for receiving and supporting in a substantially vertical position a medicament delivery device having a proximal end and a distal end with its proximal end in upright orientation. The supporting device comprises a support body having a least a first top surface facing upwardly in up-right position of the body. The first top surface is curved, bend or flat surface and has a receptive, a fixture or an accommodating depression for inserting of the medicament delivery device into it. The accommodating depression has an inner circumferential surface of a chosen shape and size and a bottom surface of a chosen shape. A second curved base surface intersects with the first top surface circumferentially thus defining the support body of the supporting device. The second curved surface is facing away from the first surface. A central axis A of the body is perpendicular to the first and the second surfaces and is vertical when the body is in its up-right position. The second surface is smooth with one of a spherical or elliptical shape without any irregularities allowing the central axis A of the body of the device to swing around a center of gravity in all directions if/when the body set in motion.

According to another aspect, there is provided a self-righting device comprising a support body for supporting a medicament delivery device; the support body having a mass, a center of gravity and a shape such that the self-righting device, when positioned on a substantially horizontal surface, moves from an unbalanced position to an upright position. The self-righting device further comprises a mechanical adaptor configured to be attached to the support body and for holding an elongated medicament delivery device at an angle less than 30 degrees from a vertical axis when the self-righting device is in the upright position. The mechanical adaptor or adaptors can be used when the medicament delivery devices of the different dimensions and shapes of the distal end are to be supported in one, became universal a supporting self-righting device. The adaptor/adaptors might have the varying reception parts for fitting the different medicament delivery devices and a size/shape of the outer circumference fitting in or mating with the accommodating depression or a fixture on the support body.

The self-righting supporting device according to the present disclosure facilitates preparation and handling of the medicament delivery device. Since the self-righting device is configured to automatically move from the unbalanced position to the upright position while holding the medicament delivery device in up-right position, it is avoided that the medicament delivery device lies flat on the horizontal surface. The self-righting supporting device thereby provides self-rightness of the medicament delivery device. The vertical or up-right positioning of the medicament delivery device by the self-righting device, i.e. at an angle less than 30 degrees from the vertical axis, prevents the medicament delivery device from rolling away on a flat surface or possibly fall down.

In addition, the vertical positioning (or substantially vertical positioning) of the medicament delivery device improves handling of the medicament delivery device since this orientation makes the medicament delivery device easy to grasp, particularly for patients with reduced hands or fingers ability to grasp. For example, a user may easier remove a cap from the medicament delivery device, even by one hand, when the device is situated vertically.

Furthermore, the vertical positioning (or substantially vertical positioning) of the medicament delivery device enables gas that appears during mixing of the multicomponent medicament to escape. Thus, the self-righting supporting device ensures that the medicament delivery device is primed and oriented in the proper position before use.

The self-righting supporting device, e.g. having the mechanical adaptor thereof, which is to be inserted into the accommodating depression or in an accommodating member and configured to hold the distal end of the medicament delivery device which is opposite to the proximal end from which the medicament delivery occurs. The dimension and shape of the outer circumference surface of the adaptor shall mate with the inner circumference surface dimension and shape of the accommodating member or fit into it, wherein the inner circumference surface dimension and shape of the adaptor shall mate the outer surface of the distal end of the supported medicament delivery device to be inserted in it. The distal ends of the different medicament delivery devices may also have the different shapes and dimensions, and therefore, the adaptor allows to use the single supporting device or the support body for supporting the different medicament delivery devices in the up-right position just by changing to the correspondent adaptor. Throughout the present disclosure, the self-righting supporting device may be referred to as a self-balancing cap or module.

The medicament delivery device may comprise an elongated tubular housing of varied cross-sectional shapes. The medicament delivery device according to the present disclosure may comprise at least two chambers for containing two medicament agents to be manually mixed before being delivered. The medicament delivery device may for example be an injection or an auto-injection device for injecting a medicament, such as a drug mixture, by a user. Alternatively, it might be an inhaler.

The support body may be generic, such that various different types of mechanical adaptors can be attached to the support body. The mechanical adaptor may be configured to hold a particular type (or a particular end) of medicament delivery device. Thus, the mechanical adaptor may be adapted for a particular type of medicament delivery device. The self-balancing cap or the support body and the adaptor(s) may be delivered together with the corresponding medicament delivery device or separately. At the change of the medicament/medicament delivery device, it is not required to obtain a new supporting device, but just to change the adaptor, which is economic and environmental advantageous.

The mechanical adaptor may be constituted by a coupler between the support body and the medicament delivery device. The mechanical adaptor may be tubular or may comprise a tubular portion. When the self-righting supporting device does not hold any medicament delivery device and when the mechanical adaptor is attached to the support body, the mechanical adaptor may be accessible in an upward direction when the self-righting device adopts the upright position. The mechanical adaptor may be provided with friction increasing material in order to more securely hold an end of the medicament delivery device.

The self-righting supporting device may be configured such that the center of gravity of the self-righting support body is positioned along a central axis at a location causing the support body to automatically orient the medicament delivery device when been supported in a substantially vertical or up-right orientation when the self-righting device is placed on a flat substantially horizontal surface. The support body and/or the mechanical adaptor may be manufactured by an injection molding, for example from thermoplastic materials.

Throughout the present disclosure, the self-righting supporting device may be a medical-use self-righting device. The self-righting device according to the present disclosure is not a toy but a useful accessory for improving a self-administration of the medicament.

The self-righting supporting device according to the present disclosure may be an accessory to the medicament delivery device purchased when/if needed. The self-righting device may for example be delivered together with the medicament delivery device as a kit.

The support body or the self-balancing cap may comprise at least a proximally-facing first surface which faces generally upwards in an upright position of the self-righting device, a distally-facing convex second surface which faces generally downwards in an upright position of the self-righting device. The second surface may comprise a continuous convex shape. That is, for each point on the second surface having a continuous convex shape, a normal to the point points in a unique direction. The second surface may not comprise any flat portion. The convex shape may be substantially hemispherical, or hemispherical. The support body may thus form a hemisphere.

The positioning of the center of gravity causes the self-righting supporting device to rock from any unbalanced position, where the second surface is in contact with the substantially horizontal surface, to the upright position. When the medicament delivery device is held such that its longitudinal axis is parallel with a vertical axis, the first surface may be horizontal, or substantially horizontal.

The center of gravity may be located between the first surface and the second surface. For example, the center of gravity may be distanced less than 40%, such as less than 15%, of a height of the self-righting device from a lowermost point of the second surface (when the self-righting device adopts the upright position).

The support body may comprise the accommodating member, and the mechanical adaptor may be shaped and dimensioned so as to securely hold a predetermined medicament delivery device to the self-righting supporting device by attachment to the accommodating member. In this case, the mechanical adaptor may be permanently attached to the accommodating member. The permanent attachment to the accommodating member may be achieved by at least one of glue, press-fit or snap-fit connection between the mechanical adaptor and the accommodating member.

Alternatively, the mechanical adaptor may hold the medicament delivery device to the self-righting supporting device by releasable attachment to the accommodating member. The releasable attachment to the accommodating member may be achieved by at least one of a threaded coupling, a bayonet coupling or a friction-fit coupling between the mechanical adaptor and the medicament delivery device, and between the mechanical adaptor and the accommodating member. Any other known releasable connection types are also can be used.

The accommodating member may be a socket in the first surface of the support body, and the center of gravity may be located between the socket bottom and the second surface. Alternatively, the accommodating member may be a fixture on the first top surface of the support body (not shown).

The support body may comprise at least one of a weight element such as e.g. a battery or a motor and the other components such as LED indicators, loudspeakers, a temperature sensor or a communication module. The motor may be used to shake the medicament delivery device for mixing the medicament for a prescribed time. Alternatively, the motor may be used to provide a status indication, for example by vibrating, swinging and/or "dancing". Also the LED indicators and the speakers may be used to provide a status indication to the user of the either mixing completion or the medicament delivery device priming completion processes or the both.

The weight element may for example be formed either by a sold piece of the support body material itself or comprise additionally a tungsten. The self-righting supporting device may comprise one or several weight elements. As its name implies, a weight element adds weight to the self-righting device. Of course, a weight element may provide further functions than only adding weight.

The support body may comprise at least a battery and a motor which motor may be activated to mix a diluent and a medicament contained in the different separate chambers of the medicament container of the medicament delivery device supported by the support body. Alternatively, or in addition, the support body may comprise at least a battery, a communication module and a motor, which communication module may, wirelessly or by direct contact, obtain a status from the medicament delivery device supported by the support body to activate the motor to perform a motion of the support body, which motion indicates the status of the medicament delivery device supported by the support body.

The support body may further comprise a communication module and at least one of a LED indicator and a speaker, which communication module may, wirelessly or by direct contact, obtain a status from the medicament delivery device supported by the support body to visibly and/or audibly indicate the status of the medicament delivery device supported by the support body to the user. In such a case, the motor or alternatively battery might function as a weight element.

According to a further aspect, there is provided a self-righting supporting device comprising a support body for supporting a medicament delivery device in the upright position; the support body having a mass, a center of gravity and a shape such that the self-righting device, when positioned on a substantially horizontal surface, moves from an unbalanced position to an upright position. The self-righting device is configured to hold the elongated medicament delivery device at an angle less than 30 degrees from a vertical axis when the self-righting device is in the upright position. Thus, the self-righting supporting device according to the present disclosure does not necessarily comprise a mechanical adaptor. The self-righting device without the mechanical adaptor is easier to manufacture, cheaper and can provide a good support for a particular type of the medicament delivery device. If the user only uses one type of medicament or the medicament delivery device, a self-righting device without a mechanical adaptor is sufficient. According to a further aspect, there is provided an assembly of the self-righting device according to the present disclosure, and an elongated medicament delivery device to be supported. The medicament delivery device may comprise a temperature sensor e.g. as a chip or another kind of sensors at its distal end attached to the support body and the self-righting device may comprise a communication module for reading temperature data from the chip of the temperature sensor or the other data. The medicament delivery device supporting body may have a memory or be able to communicate with the other devices e.g. a computer and suitable gadgets in a known manner for transferring or recording of data.

BRIEF DESCRIPTION OF THE FIGURES

Further details, advantages and aspects of the present disclosure will become apparent from the following embodiments taken in conjunction with the drawings, wherein.

DETAILED DESCRIPTION

Figure 1:
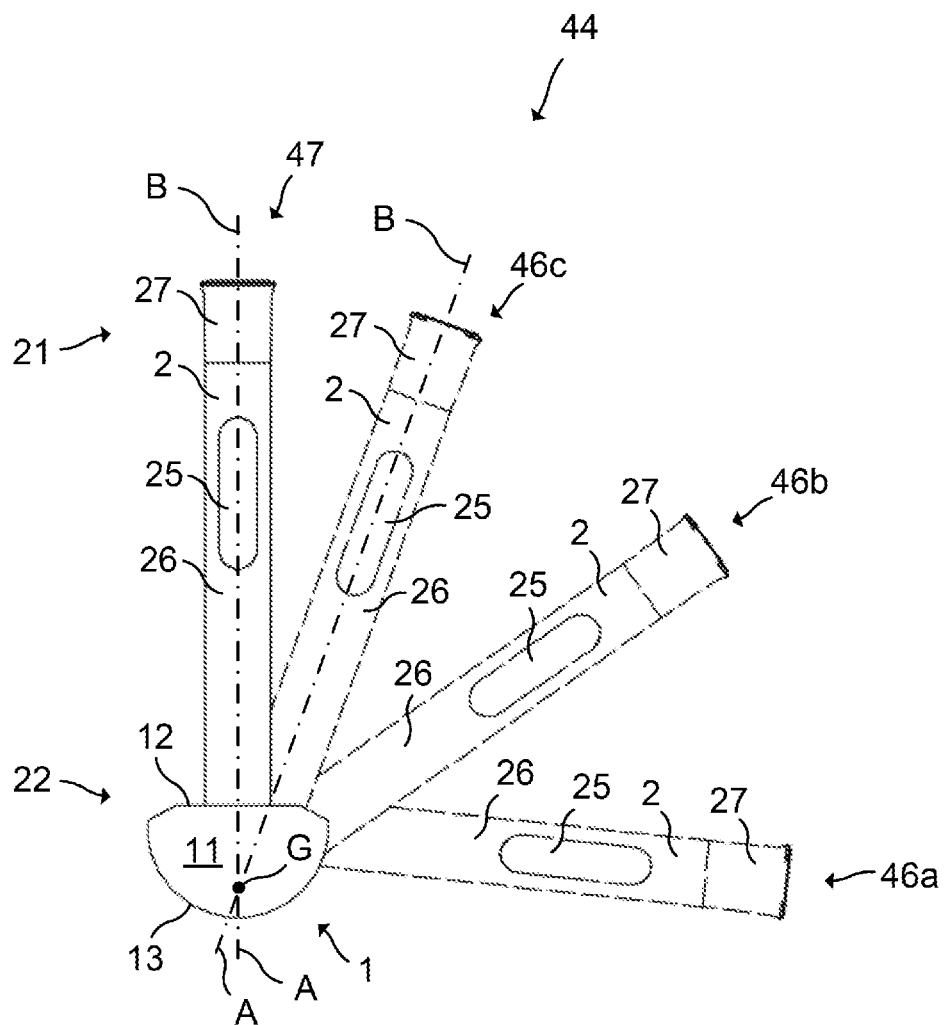
FIG. 1 schematically represents a side view of an assembly comprising a self-righting device and a medicament delivery device held by the self-righting device in various different positions.

In the following, a self-righting device comprising a support body for supporting a medicament delivery device, which might be a manual injector, an automatic or semi-automatic injector or an inhaler, and an assembly comprising a self-righting device and an elongated medicament delivery device, will be described. The same reference numerals will be used to denote the same or similar structural features.

FIG. 1 schematically represents a side view of an assembly 44 comprising a self-righting device 1 and a medicament delivery device 2. The medicament delivery device 2 is held by the self-righting supporting device 1. The medicament delivery device 2 is elongated along longitudinal axis B and has a proximal end 21 and a distal end 22. The self-righting device 1 comprises a support body 11. The support body 11 has a central axis A. When the medicament delivery device 2 is held by the self-righting device 1, the longitudinal axis B of the medicament delivery device 2 is coincident, or substantially coincident, with the central axis A of the support body 11. As shown in FIG. 1, the self-righting device 1 supports the distal end 22 of the medicament delivery device 2.

The medicament delivery device 2 of this example comprises an elongated tubular housing 26 and a cap 27 attached to the housing 26 at the proximal end 21 thereof. The medicament delivery device 2 further comprises an opening 25 on its side surface for viewing a syringe. In the example in FIG. 1, the medicament delivery device 2 is an injection device.

The support body 11 has a mass and a center of gravity G. The support body 11 comprises a proximally-facing first top surface 12 and a distally-facing opposite second base surface 13. The center of gravity G of the support body 11 is positioned between the first surface 12 and the second surface 13. In the example in FIG. 1, the second surface 13 is evenly convex and hemispherical. The second surface 13 has a smooth shape without any flat portions or irregular portions. Furthermore, the second surface 13 is rotationally symmetric with respect to the central axis A.

The mass, the center of gravity G and the shape of the support body 11 thereby causes the support body 11, when holding the medicament delivery device 2, to move from any of unbalanced positions 46a, 46b, 46c on a substantially horizontal surface to an upright position 47. The self-righting device 1 thus prevents the medicament delivery device 2 from laying horizontally in the unbalanced position 46a. In the upright position 47, the proximal end 21 of the medicament delivery device 2 is directed upwards.

The gravity force of the self-righting device 1 generates a moment on the self-righting device 1 and on the medicament delivery device 2 such that the self-righting device 1, and the medicament delivery device 2 held by the self-righting device 1, are rotated from any of the unbalanced position 46a, 46b, 46c, towards the upright position 47. The self-righting device 1 and medicament delivery device 2 will eventually become stable and at rest in the upright position 47. However, the hemispherical shape of the support body 11 causes the self-righting device 1 to swing back and forth before becoming stable and at rest in the upright position 47.

Figure 2:
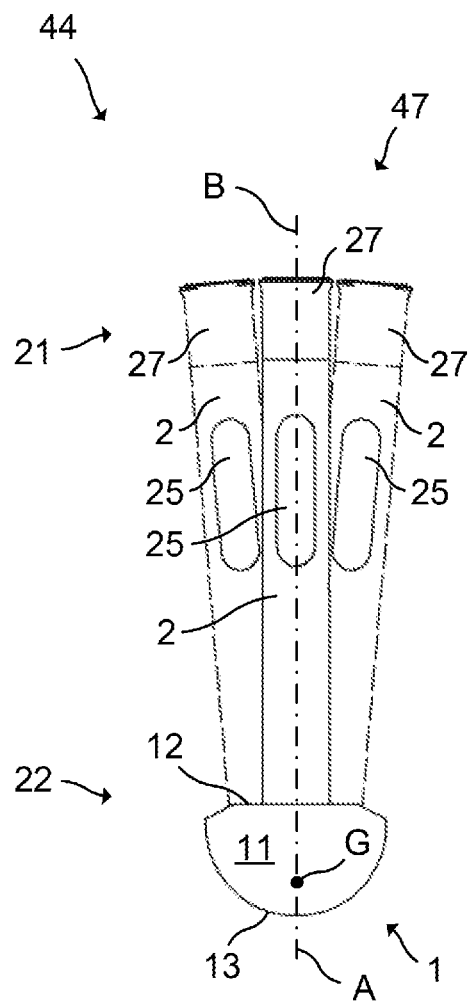
FIG. 2 schematically represents a side view of the medicament delivery device held by the self-righting device in various different upright positions.

FIG. 2 schematically represents a side view of the medicament delivery device 2 held by the self-righting supporting device 1 in various different upright positions 47. As can be seen in FIG. 2, in the upright position 47 of the self-righting device 1, the first surface 12 faces generally upwards and the second surface 13 faces generally downwards. In each upright position 47 of the self-righting device 1, the medicament delivery device 2 is held such that the longitudinal axis B of the medicament delivery device 2 and the central axis A of the self-righting device 1 are less than 30° from a vertical axis.

Prior to delivering a dose of medicament, a user may for example remove the cap 27 and initiate mixing of two medicament components. The mixing process may be initiated in various ways, for example by pushing a button, rotating two parts relative to each other or releasing a lock. When the mixing has been initiated, a first chamber of a medicament container containing a medicament agent and a second chamber of the medicament container containing a diluent are brought into communication. When the medicament agent and the diluent are mixed, air bubbles often develop. In order to release these bubbles, the medicament delivery device 2 should be held in an upright position, preferably in substantially vertical orientation for some time that might be different for different medicaments, for example a few minutes. As known, this process is called priming. The self-righting supporting device 1 assists in priming for a user that do not need to hold the medicament delivery device in a hand by supporting the medicament delivery device 2 in a generally vertical orientation and by swinging about its axis.

When the mixing has been initiated, the medicament delivery device 2 may be inserted by the user into the self-righting device 1. The user might be a patient itself or medically trained personnel. Alternatively, mixing of the medicament delivery device 2 may be initiated while already being supported by the self-righting supporting device 1. When the mixing has been initiated, the user may place the assembly 44 on a substantially horizontal surface, such as on a table surface. Unless the medicament delivery device 2 is placed in a perfectly vertical orientation, the self-righting device 1 and the medicament delivery device 2 will swing slightly about a vertical axis. This swinging enhances the mixing, e.g. by making the mixing more homogenous and/or by more efficiently venting gases.

Figures 3, 4, 5:
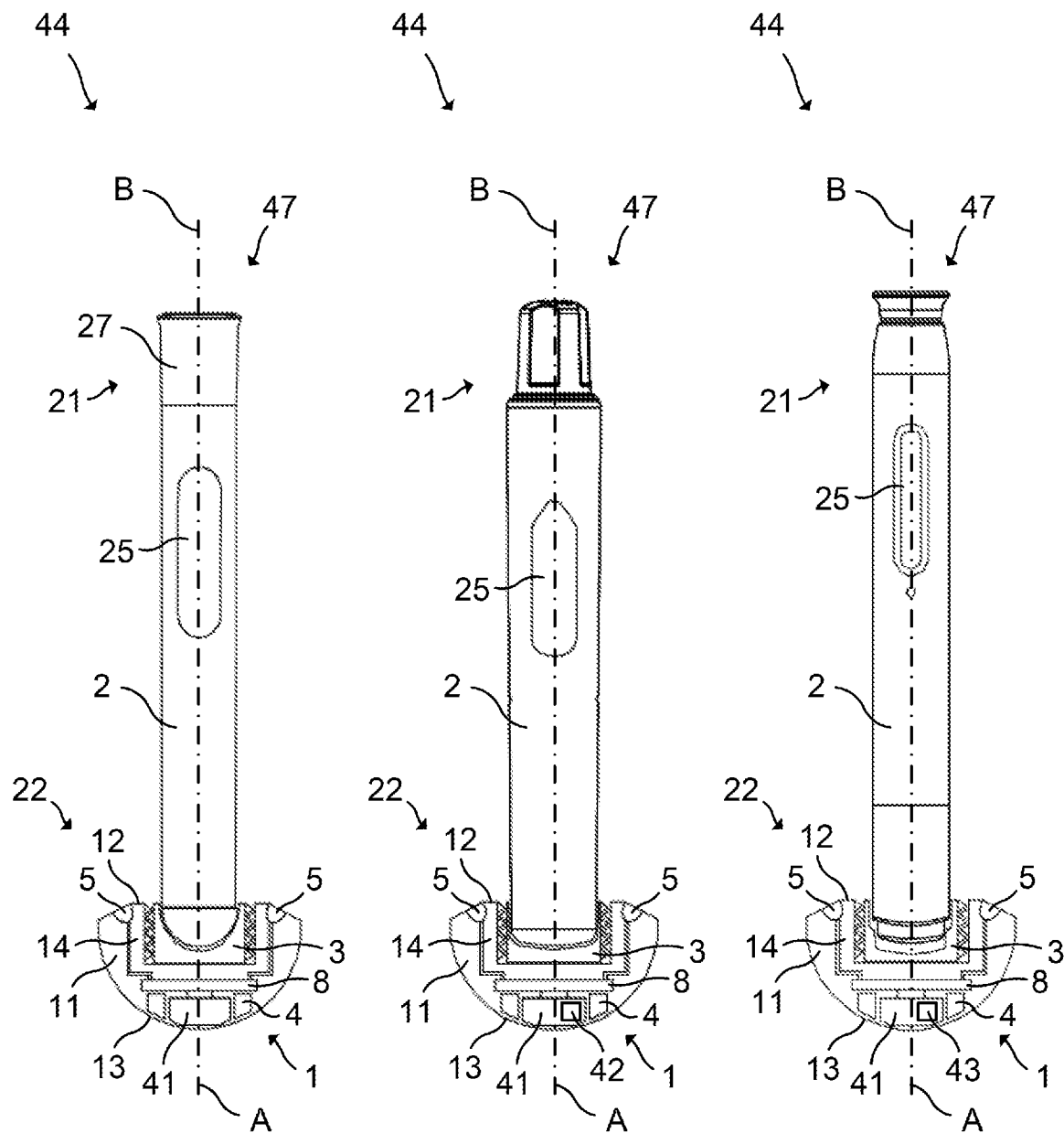
FIG. 3 schematically represents a cross section view of the self-righting device in the assembly in FIGS. 1 and 2.
FIG. 4 schematically represents a cross section view of the self-righting device in a further assembly comprising an alternative medicament delivery device held by an alternative self-righting device.
FIG. 5: schematically represents a cross section view of the self-righting device in a further assembly comprising an alternative medicament delivery device held by an alternative self-righting device.

FIG. 3 schematically represents a side view of the assembly 44 in FIGS. 1 and 2. The self-righting device 1 is shown in cross-section. The medicament delivery device 2 self-righting supporting device 1 comprises a mechanical adaptor 3. An upper surface of the mechanical adaptor 3 is flush with the first surface 12 of the support body 11 as illustrated. Alternatively, the mechanical adaptor may extend over the top surface 12 (not shown) e.g. for a better grasp by fingers and an easier exchange of the adaptors. The mechanical adaptor 3 is configured to be attached to the support body 11. Furthermore, the mechanical adaptor 3 is configured to hold the distal end 22 of the medicament delivery device 2. As shown in FIG. 3, the distal end 22 of the medicament delivery device 2 and a corresponding opening in the mechanical adaptor 3 are each generally hemispherical and mating each other for secure holding.

The self-righting device 1 of the example in FIG. 3 further comprises an optional accommodating member 14. The accommodating member may form a fixture on the first surface 12 of the support body 11 (not shown) or alternatively an opening 14 as illustrated in FIG. 3. The mechanical adaptor 3 is shaped and dimensioned so as to securely hold the medicament delivery device 2 to the self-righting supporting device 1. In the example in FIG. 3, the accommodating member 14 is integrally formed with the support body 11 as the opening 14. However, alternatively the accommodating member 14 might be permanently attached to the support body 11 (not shown).

The self-righting supporting device 1 in FIG. 3, further comprises a weight element 4. In this example, the weight element 4 is annular and concentric with the central axis A of the support body 11. The weight element 4 is positioned in a lower portion of the support body 11 along its central axis A such that the center of gravity G of the self-righting device 1 is lowered. In this example, the weight element 4 surrounds or alternatively comprises a battery 41. The weight element 4 in FIG. 3 is merely one of many possible variants.

The self-righting supporting device 1 of the example in FIG. 3 further comprises the battery 41, a PCB (printed circuit board) 8 and LED (light emitting diode) indicators 5 powered by the battery 41. The LED indicators 5 may for example be used to indicate when mixing is completed, e.g. blink and/or change color after a certain time. In this example, the LED indicators 5 are provided in a chamfered portion adjoining the first surface 12 and the second surface 13. The LED indicators can be a number of separate LED elements for providing indications for different medicament delivery statuses or alternatively the LED element might be a single element and/or ring-formed indicator.

FIG. 4 schematically represents a side view of a further assembly 44 comprising an alternative medicament delivery device 2 held by an alternative self-righting supporting device 1. Mainly differences with respect to FIG. 3 will be described below.

The distal end 22 of the medicament delivery device 2 in FIG. 4 has a more planar profile than in FIG. 3. Accordingly, the mechanical adaptor 3 has an opening with a corresponding mating profile. The mechanical adaptor 3 may be replaced in order to hold medicament delivery devices 2 having distal ends 22 of various shapes and/or sizes.

The self-righting supporting device 1 of the example in FIG. 4 further comprises a communication module 42. The communication module 42 may be an RFID (Radio Frequency Identification) device, a Wi-Fi device or a BLE (Bluetooth Low Energy) device. The communication module 42 may be used for wirelessly reading information from the medicament delivery device 2 having a chip at its distal end, such as serial number, batch number etc. This may for example be useful if a manufacturer wants to recall a particular batch of a medicament. Alternatively, or in addition, the communication module 42 may be used for communicating with a smart phone or a computer for recording the time, a dose or frequency of the medicament deliveries.

FIG. 5 schematically represents a side view of a further assembly 44 comprising an alternative medicament delivery device 2 held by another alternative self-righting supporting device 1. Mainly differences with respect to FIGS. 3 and 4 will be described below.

The distal end 22 of the medicament delivery device 2 in FIG. 5 has a stepped profile, i.e. an upper (or proximal) relatively large diameter section and a lower (or distal) relatively small diameter section. The mechanical adaptor 3 attached to the accommodating member 14 in FIG. 5 has a corresponding stepped mating profile.

The self-righting supporting device 1 in FIG. 5 further comprises a motor 43. The motor 43 is powered by the battery 41. The motor 43 may be used to vibrate or shake the self-righting device 1 for a predetermined time. These vibrations from the motor 43 in combination with the self-righting effect of the self-righting supporting device 1 provide an improved mixing of a diluent and a medicament contained separately in the medicament delivery device 2, when this is supported by the support body 11. Alternatively, the shaking might be required for e.g. the inhaler prior to discharging of a medicament. The motor 43 thus functions as an agitator that shakes the self-righting device 1 and the inserted into it the medicament delivery device 2 for more efficiently mixing the diluent and the medicament and achieving a more homogeneous medicament.

Figure 6:
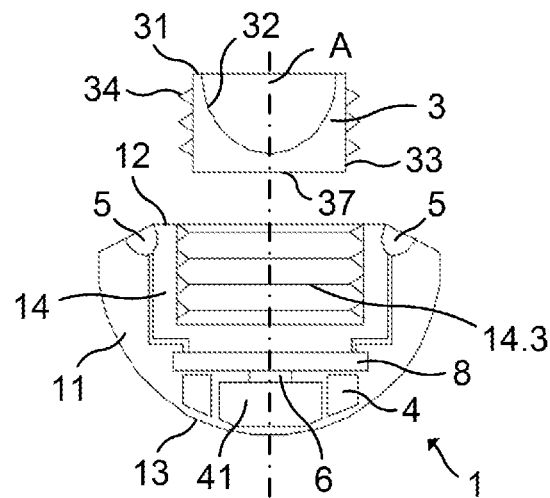
FIG. 6 schematically represents a detailed cross-sectional view of the self-righting device in FIG. 4 in a disassembled state with an adaptor.
Figure 7:
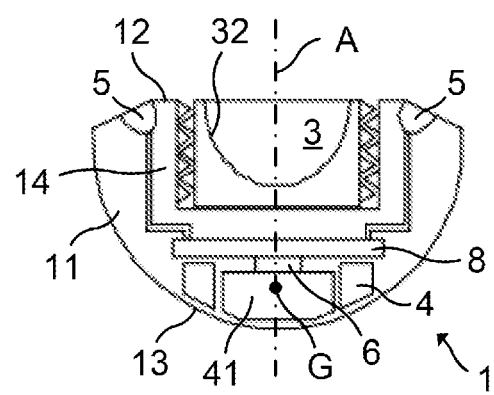
FIG. 7 schematically represents the self-righting device 1 in FIG. 6 in an assembled state.

FIG. 6 schematically represents a cross-sectional view of the self-righting supporting device 1 in FIG. 4 in a disassembled state. FIG. 7 schematically represents the self-righting device 1 in FIG. 6 in an assembled state. With collective reference to FIGS. 6 and 7, the mechanical adaptor 3 comprises a circumferential wall 31. The mechanical adaptor 3 further comprises a female profile 32. The shape of the female profile 32 is generally hemispherical and corresponds to the shape of the distal end 22 of the medicament delivery device 2. Under the female profile 32 can be placed speakers 6 and/or a temperature sensor 7 (not illustrated).

FIG. 6 shows that the circumferential wall 31 of the mechanical adaptor 3 comprises a cylindrical external side surface 33 and a flat external bottom surface 37. The mechanical adaptor 3 thus forms a socket in the first surface 12 of the support body 11 (when inserted therein). The mechanical adaptor 3 comprises an external thread 34 on the external side surface 33 for threadingly engaging an internal thread 14.3 in the accommodating member 14, which is here illustrated as an opening. The mechanical adaptor 3 can thus be attached to the support body 11 by screwing the mechanical adaptor 3 into the accommodating member 14, as shown in FIG. 7. The mechanical adaptor 3 may then be replaced with an alternative mechanical adaptor 3 comprising a different female profile 32 but the same type of external thread 34. Thus, the mechanical adaptor 3 is releasably attached to the accommodating member 14 by means of a threaded coupling.

Figure 8:
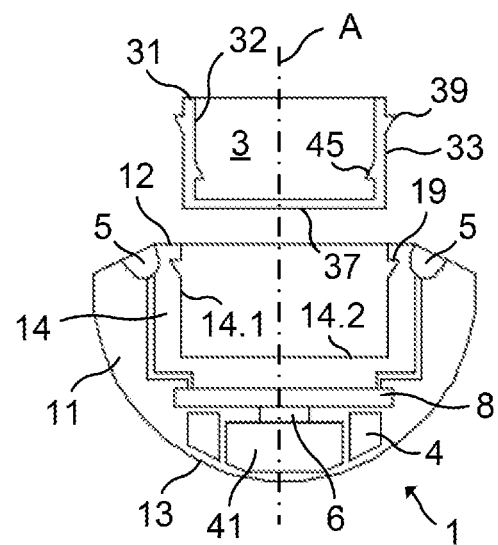
FIG. 8 schematically represents a cross-sectional exploded view of an alternative self-righting device in a disassembled state with a different form of the adaptor.
Figure 9:
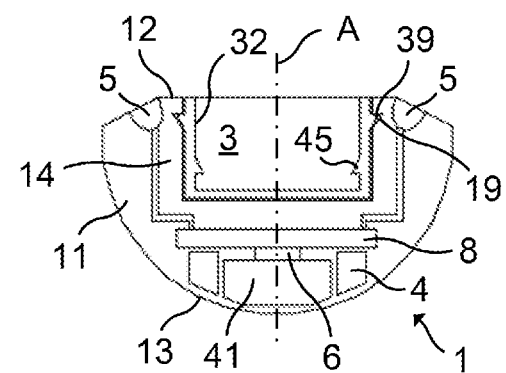
FIG. 9: schematically represents the self-righting device in FIG. 8 in an assembled state.

FIG. 8 schematically represents a cross-sectional exploded view of an alternative self-righting device 1 in a disassembled state. FIG. 9 schematically represents the self-righting device 1 in FIG. 8 in an assembled state. Mainly differences with respect to FIGS. 6 and 7 will be described. Instead of being generally hemispherical, the female profile 32 of the mechanical adaptor 3 in FIGS. 6 and 7 is cylindrical.

Instead of the external thread 34 in FIG. 6, the mechanical adaptor 3 in FIG. 8 comprises external protrusions 39 on the external side surface 33. The mechanical adaptor 3 in FIG. 8 comprises four external protrusions 39, but the number may vary. At least one external protrusion 39 may be provided. Each external protrusion 39 is illustrated as a wedge-shaped but any other forms and suitable shape are also possible.

The mechanical adaptor 3 in FIG. 8 further comprises internal protrusions 45 on the surface of the female profile 32. The mechanical adaptor 3 in FIG. 8 comprises four internal protrusions 45, but the number may vary. At least one internal protrusion 45 may be provided. The internal protrusions 45 are used to more securely engage a distal end 22 of a medicament delivery device 2.

As shown in FIG. 8, the accommodating member 14 comprises a cylindrical interior wall 14.1 and a bottom surface 14.2. A recess 19 receiving the external protrusion 39 of the mechanical adaptor 3 is provided (only two are visible in FIG. 8) in the interior wall 14.1. In this example, the recess 19 is annular.

Although the mechanical adaptor 3 in FIGS. 6 and 7 comprising an external thread 34 has to have a circular circumference, the mechanical adaptor 3 in FIG. 8 may have a wide range of cross-sectional profiles (i.e. transverse to the central axis A of the self-righting device 1) including circular, oval, triangular, and other polygonal profiles. The same applies for the interior wall 14.1 of the accommodating member 14.

As shown in FIG. 9, when inserting the mechanical adaptor 3 into the accommodating member 14, the external protrusions 39 engage the recess 19 such that the mechanical adaptor 3 is locked to the accommodating member 14. Thereby, the mechanical adaptor 3 is permanently attached to the accommodating member 14 by means of a snap-fit connection.

Figure 10:
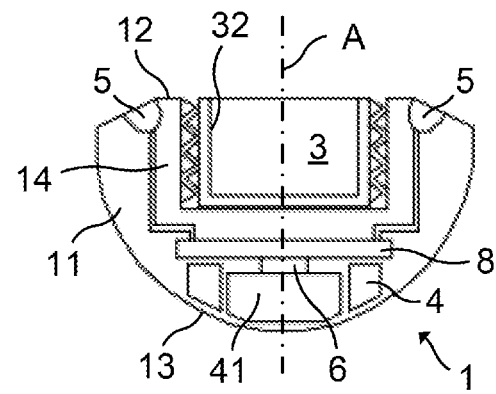
FIG. 10 schematically represents a cross-sectional view of an alternative self-righting device in an assembled state with the adaptor.

FIG. 10 schematically represents a cross-sectional view of an alternative self-righting supporting device 1. The self-righting device 1 in FIG. 10 differs from the self-righting device 1 in FIGS. 6 and 7 in that female profile 32 is cylindrical instead of hemispherical.

Figure 11:
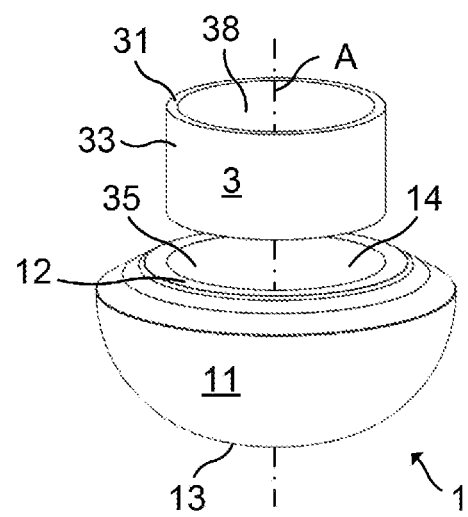
FIG. 11: schematically represents a perspective view of a further alternative self-righting device in a disassembled state with a still another kind of adaptor.

FIG. 11 schematically represents a perspective view of a further alternative self-righting device 1 in a disassembled state. Mainly differences with respect to FIGS. 4 and 5 will be described. The cylindrical mechanical adaptor 3 of the self-righting device 1 in FIG. 11 comprises a through opening 38 and a circumference wall 31. Furthermore, the external side surface 33 of the circumferential wall 31 is smooth. The mechanical adaptor 3 is connected to the accommodating member 14 of the support body 11 by means of glue 35 layer or alternatively by a press-fit connection.

Figure 12:
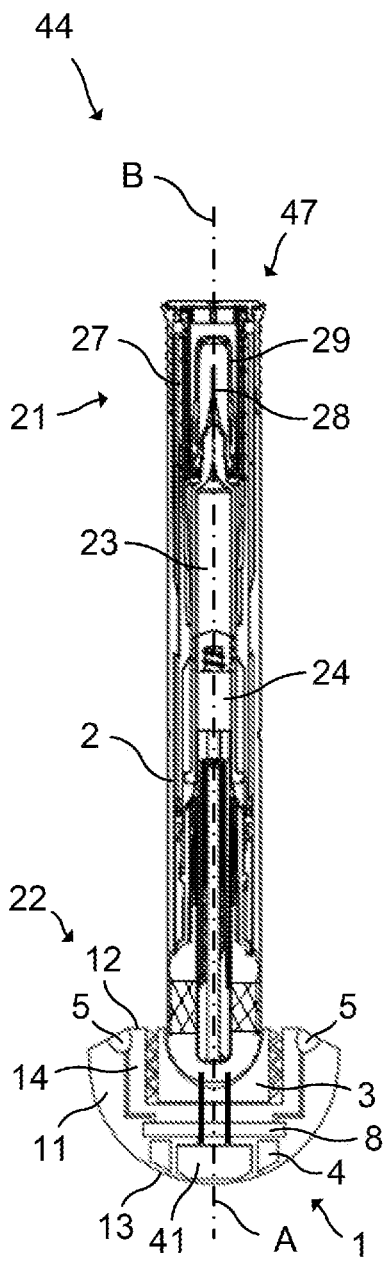
FIG. 12 schematically represents a cross-sectional view of the assembly in FIG. 3.

FIG. 12 schematically represents a cross-sectional view of the assembly 44 in FIG. 3. FIG. 12 shows that the medicament delivery device 2 comprises a syringe 23 with a medicament, a stopper 24, a needle 28 and a needle shield 29. As can be seen in FIG. 12, the needle 28 points upwardly, towards the proximal end 21 of the medicament delivery device 2. This orientation of the medicament delivery device 2 enables air bubbles or gases to escape during mixing or priming.

Figure 13:
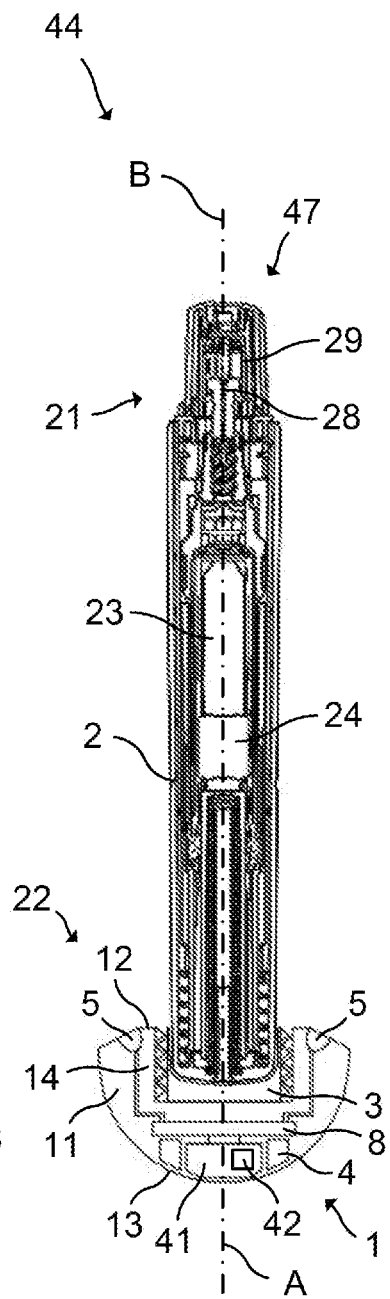
FIG. 13 schematically represents a cross-sectional view of the assembly in FIG. 4.
Figure 14:
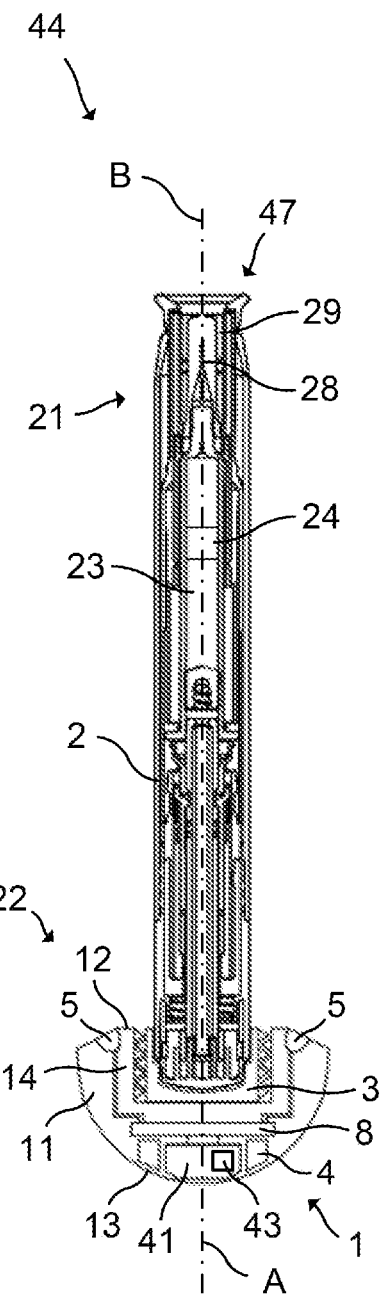
FIG. 14: schematically represents a cross-sectional view of the assembly in FIG. 5.

FIG. 13 schematically represents a cross-sectional view of the assembly 44 in FIG. 4 and FIG. 14 schematically represents a cross-sectional view of the assembly 44 in FIG. 5.

Figure 15:
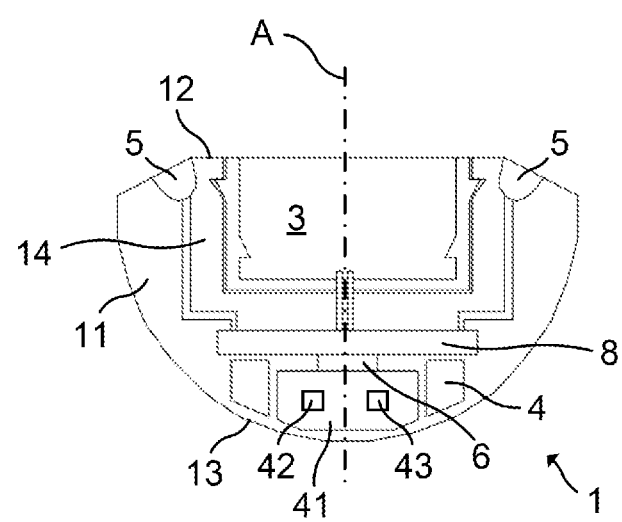
FIG. 15 schematically represents a cross sectional side-view of a further example of a self-righting device.

FIG. 15 schematically represents a cross sectional side-view of a further example of a self-righting supporting device 1. The self-righting supporting device 1 in FIG. 15 comprises the same type of snap-fit connection as in FIGS. 8 and 9. However, the support body 11 comprises a battery 41 together with both a communication module 42 and a motor 43. The communication module 42 may, wirelessly or by direct contact, obtain a status from a medicament delivery device 2 supported by the support body 11. In response to a particular status, the motor 43 may be may be activated to perform a movement of the support body 11 and thus shaking of the medicament delivery device 2. The movement may be a vibration of the support body 11 in response to a status indicating initiated mixing. Alternatively, or in addition, the movement may be a vibration of the support body 11 to indicate completed mixing. The motor 43 may induce a vibration of the support body 11 such that the entire assembly 44 "dances" on the substantially horizontal surface. This function might be used for a medicament delivery device with a container having a single medicament chamber which does not require the mixing of two components; on the other hand it might be advantageous for medicaments requiring to be shaken prior to use.

The self-righting supporting device 1 in FIG. 15 further comprises a speaker 6 situated under the PCB 8. By means of the LED indicators 5 and the speaker 6, the self-righting device 1 may visibly and/or audibly indicate a status of the medicament delivery device 2, supported by the support body 11, e.g. amount of the delivered medicament, time of the delivery, amount of the doses which might be left for a multi-dose delivery device and the like information.

Figure 16:
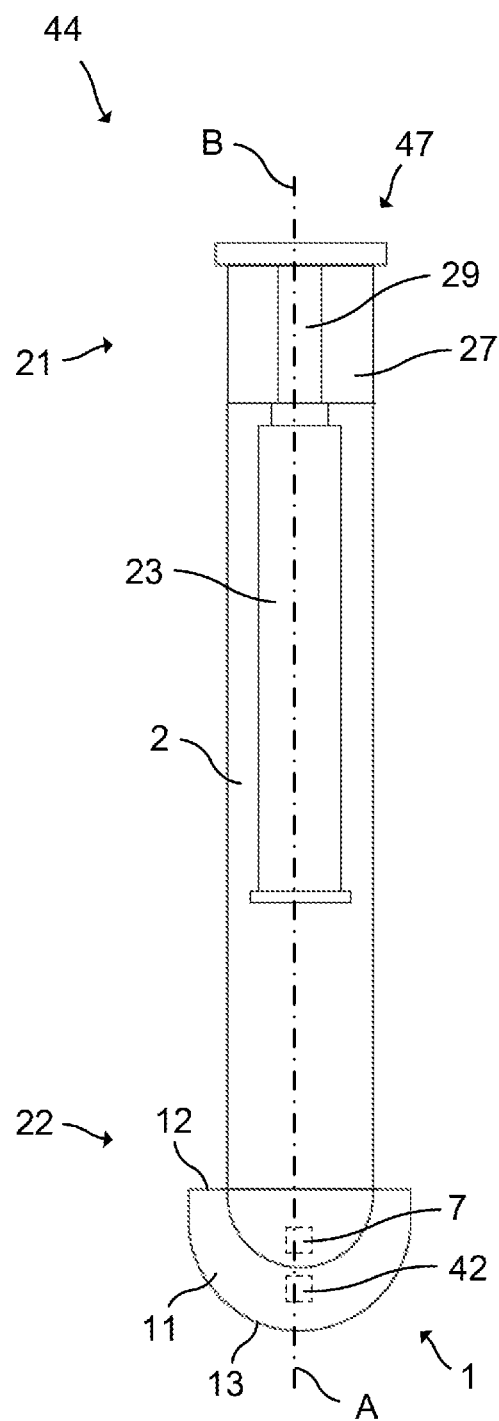
FIG. 16 schematically represents a cross-sectional view of a further assembly comprising an alternative medicament delivery device held by an alternative self-righting device.

FIG. 16 schematically represents a cross-sectional view of a further assembly 44 comprising an alternative medicament delivery device 2 held by an alternative self-righting supporting device 1. The medicament delivery device 2 self-righting supporting device 1 of this example comprises a temperature sensor 7. The medicament delivery device 2 of this example comprises a communication module 42 for reading temperature data from the temperature sensor 7. The communication module 42 may for example be constituted by an RFID reader for reading an RFID tag of the temperature sensor 7 in the medicament delivery device 2. The self-righting device 1 may be configured to indicate a temperature status of the medicament delivery device 2 based on the read temperature data. For example, the self-righting device 1 may be configured to perform a movement and/or issue an audible and/or visual alarm based on the temperature data, such as when a medicament contained in the medicament delivery device 2 has reached a target temperature range (e.g. room temperature) or when the temperature exceeds or lower a reference temperature. Alternatively, the sensor 7 situated optionally at the distal end of the medicament delivery device 2, as illustrated, might be the other types of sensors or a chip 7 indicating a medicament, manufacturer, batch number and the like for easier identification of a drug, dose etc and transferring this information to the communication module 42, which in its turn might transfer this data to a external receiver such as a computer or another suitable gadget.

While the present disclosure has been described with reference to exemplary embodiments, it will be appreciated that the present invention is not limited to what has been described above. For example, it will be appreciated that the dimensions of the parts such as the accommodating member 14 of the support body 11 and the distal end 22 of the medicament delivery device 2 may be adapted to each other to mate as needed and the adapter 3 might be omitted as illustrated in FIG. 16.

The invention claimed is:

1. A supporting device for a medicament delivery device, the supporting device comprising:
a support body for supporting the medicament delivery device, where the support body has a mass, a center of gravity G and a shape such that when positioned on a substantially horizontal surface the support body moves from an unbalanced position to an upright position, where the supporting device is a self-righting device and where the support body further comprises at least:
a proximally facing first surface which faces generally upwards in an upright position of the self-righting device;
a distally facing convex second surface which faces generally downwards in an upright position of the self-righting device and is configured to contact the substantially horizontal surface;
an accommodating member defining an opening in the first surface;
a socket defined by an internal portion a mechanical adaptor that is accepted through the opening in the accommodating member such that the socket has a bottom that is located above the second surface such that the center of gravity is below the bottom of the socket and above the second surface; and
a central axis A of symmetry substantially perpendicular to the first and second surfaces,
wherein the mechanical adaptor is inserted or removed from the accommodating member by a user of the medicament delivery device, and
wherein the socket comprises a mating profile that cooperates and engages with a corresponding mating profile on a distal end of the medicament delivery device to securely hold the medicament delivery device before or after the mechanical adaptor is inserted into the accommodating member.

2. The supporting device according to claim 1, wherein the mechanical adaptor further comprises an external side surface comprising a first connector that engages a second connector in the accommodating member to form a releasable attachment to the accommodating member, where the releasable attachment is achieved by at least one of a threaded coupling, a bayonet coupling or a friction-fit coupling.

3. The supporting device according to claim 1, wherein the accommodating member is attached to the supporting device by permanent attachment.

4. The supporting device according to claim 1, wherein the support body further comprises at least one of a weight element, a battery, a motor, LED indicators, speakers, a temperature sensor or a communications module.

5. The supporting device according to claim 1, wherein the support body further comprises at least a battery and a motor, where the motor may be activated to mix a diluent and a medicament contained in a medicament delivery device supported by the support body.

6. The supporting device according to claim 1, wherein the support body further comprises at least a battery, a communications module and a motor, where the communications module through a wireless or direct contact obtain a status from a medicament delivery device supported by the support body to activate the motor to perform a movement of the support body, which movement indicates the status of the medicament delivery device supported by the support body.

7. The supporting device according to claim 1, where the support body further comprises a battery, a communications module and at least an LED indicator or a speaker, where the communications module through a wireless or direct contact obtain a status from a medicament delivery device supported by the support body to visibly or audibly indicate a status of the medicament delivery device supported by the support body.

8. An assembly of a self-righting supporting device and a medicament delivery device comprising:
an elongated medicament delivery device, having a longitudinal axis B, wherein the medicament delivery device has a proximal end and a distal end;
a mechanical adaptor comprising an external side surface and a socket having a mating profile that cooperates and engages with a corresponding mating profile on the distal end of the medicament delivery device to securely hold the medicament delivery device before the mechanical adaptor is inserted into the self-righting supporting device; and a self-righting supporting device comprising:
- a support body for supporting the medicament delivery device;
- a mass, a center of gravity and a shape such that when the support body is positioned on a substantially horizontal surface the support body moves from an unbalanced position to an upright position;
- a proximally-facing first surface which faces generally upwards in an upright position of the self-righting supporting device;
- an accommodating member defining an opening in the first surface; and
- a distally-facing convex second surface which faces generally downwards in an upright position of the self-righting supporting device and is configured to contact the substantially horizontal surface, where the second surface is a smooth hemispherical surface that does not comprise any flat portions and is rotationally symmetric with respect to a central axis A of symmetry that is substantially perpendicular to the first and second surfaces, wherein the mechanical adaptor that is accepted through the opening in the accommodating member such that a bottom of the socket is located above the second surface and the center of gravity is below the bottom of the socket and above the second surface, and wherein the external side surface comprises a first connector that engages a second connector in the accommodating member to form a releasable attachment to the accommodating member.

9. The assembly according to claim 8, wherein the medicament delivery device with the mechanical adaptor attached is configured for insertion coaxially into the accommodating member of the support body so as the proximal end of the medicament delivery device is pointing upwards.

10. The assembly according to claim 8, wherein the support body further comprises at least one of a weight element, a battery, a tungsten, LED indicators, loudspeakers, a temperature sensor, a chip with related data, a memory and a communication module able to communication with an external device or a combination thereof.

11. The assembly according to claim 8, wherein the support body further comprises a motor configured for one of a status indicator by vibrating, agitating or swinging about the axis B and shaking the medicament delivery device.

* * * * *